(12) United States Patent
Chou et al.

(10) Patent No.: US 8,709,352 B2
(45) Date of Patent: Apr. 29, 2014

(54) HUMIDITY INDICATOR AND METHOD FOR FABRICATING THE SAME

(75) Inventors: Tzu-Chi Chou, Taichung (TW);
Ren-Der Jean, Hsinchu (TW);
Hsin-Hung Pan, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 112 days.

(21) Appl. No.: 13/085,851

(22) Filed: Apr. 13, 2011

(65) Prior Publication Data

US 2012/0167816 A1    Jul. 5, 2012

(30) Foreign Application Priority Data

Dec. 31, 2010  (TW) ............................... 99147216 A

(51) Int. Cl.
*B65B 57/00* (2006.01)
*G01D 11/00* (2006.01)
*B32B 15/04* (2006.01)

(52) U.S. Cl.
USPC ............. 422/400; 422/430; 53/507; 116/200; 428/351

(58) Field of Classification Search
USPC ............ 422/50, 400, 430, 119; 53/507; 55/DIG. 34; 116/200; 428/351, 913; 73/29.01, 73
See application file for complete search history.

(56) References Cited

U.S. PATENT DOCUMENTS

| | | | |
|---|---|---|---|
| 2,460,065 A | 1/1949 | Davis | |
| 2,460,067 A | 1/1949 | Davis | |
| 2,460,069 A | 1/1949 | Davis | |
| 2,460,070 A | 1/1949 | Davis | |
| 2,460,071 A | 1/1949 | Davis | |
| 2,460,072 A | 1/1949 | Davis | |
| 2,460,073 A | 1/1949 | Davis | |
| 2,460,074 A | 1/1949 | Davis | |
| 4,909,179 A | 3/1990 | McBride | |
| 6,663,679 B1 | 12/2003 | Duncan | |
| 6,698,378 B1 | 3/2004 | Dick et al. | |
| 6,753,184 B1 | 6/2004 | Moreton et al. | |
| 6,884,394 B1 * | 4/2005 | Hehenberger et al. | 422/404 |
| 6,927,063 B2 | 8/2005 | Moreton et al. | |
| 2009/0124497 A1 | 5/2009 | Nakatsubo et al. | |

FOREIGN PATENT DOCUMENTS

WO    WO2009/157395 A1    12/2009

* cited by examiner

*Primary Examiner* — Monzer R Chorbaji
(74) *Attorney, Agent, or Firm* — Muncy, Geissler, Olds & Lowe, P.C.

(57) ABSTRACT

The disclosure provides a humidity indicator and a method for fabricating the same. The humidity indicator includes a substrate, and a composite disposed on a predetermined region of the substrate. The composite includes a hydrophilic polymer and a Ni-containing compound. The humidity indicators of the disclosure are reusable, halide-free, and cobalt-free, meeting the requirement of environmental friendliness.

5 Claims, 2 Drawing Sheets

HUMIDITY INDICATOR AND METHOD FOR FABRICATING THE SAME

CROSS REFERENCE TO RELATED APPLICATIONS

This application is based upon and claims the benefit of priority from the prior Taiwan Patent Application No. 099147216, filed on Dec. 31, 2010, the entire contents of which are incorporated herein by reference.

BACKGROUND

1. Technical Field

The disclosure relates to an indicator and method for fabricating the same, and in particular relates to a Ni-containing indicator and method for fabricating the same.

2. Description of the Related Art

A humidity indicating card (or a humidity indicator) is used for many purposes including, determining the relative humidity in shipping containers and packages, such as packaged electronics and telecommunication products. The humidity indicator cards are typically impregnated with a humidity sensitive composition and dried. Most humidity indicating cards made today use cobalt chloride as the indicator, which changes color based on the level of hydration of the cobalt chloride. Cobalt chloride is, however, a very toxic chemical compound and the European Union classified cobalt chloride as a category 2 carcinogen (Council Directive 67/548/EEC). In the Commission Directive 2004/73/EC (Apr. 29, 2004), cobalt chloride is listed as a chemical substance which may cause cancer by inhalation at concentrations of 100 ppm or higher. Thus, cobalt chloride humidity indicators have limited applications, and it is necessary to find alternate materials to replace cobalt chloride as a humidity-indicating medium.

U.S. Pat. No. 2,460,072 and U.S. Pat. No. 2,460,067 disclose using copper(I) chloride and copper(II) bromide, respectively, but these compounds are not considered suitable candidates for a commercial silica gel-based humidity indicator because of potential toxicity and environmental considerations.

U.S. Pat. No. 6,663,679 discloses a device for monitoring humidity, including a first layer, which is a visual indicator, and a second layer covering and obscuring the first layer, wherein the second layer includes a deliquescent material. The deliquescent material picks up moisture and dissolves itself in the moisture, becoming transparent and exposing the first layer. However, the device is a non-reversing humidity indicator.

U.S. Pat. No. 6,753,184, and U.S. Pat. No. 6,927,063 disclose iron salts as an alternate humidity-indicating media. These humidity-indicating media, however, have a color change that is not very distinctly detectable.

There remains a need for an improved humidity indicator that provides easy detectable color changes and is non-toxic.

SUMMARY

An exemplary embodiment of a humidity indicator includes a substrate; and a composite disposed on a predetermined region of the substrate, wherein the composite includes a hydrophilic polymer, and a Ni-containing compound.

Further, the disclosure also provides a method for fabricating the aforementioned humidity indicator, including: preparing an aqueous solution containing a Ni-containing compound; adding a hydrophilic polymer or a solution containing the hydrophilic polymer into the aqueous solution containing the Ni-containing compound, obtaining a composition; coating the composition on a substrate; and drying the substrate.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

The disclosure provides a reusable, halide-free, and cobalt-free humidity indicator, meeting the requirements of environmental friendliness. The humidity indicator produces a color change after exposure to water.

The humidity indicator of the disclosure includes a substrate, and a composite disposed on the predetermined region of the substrate, wherein the composite includes a hydrophilic polymer, and a Ni-containing compound.

Figure 1:
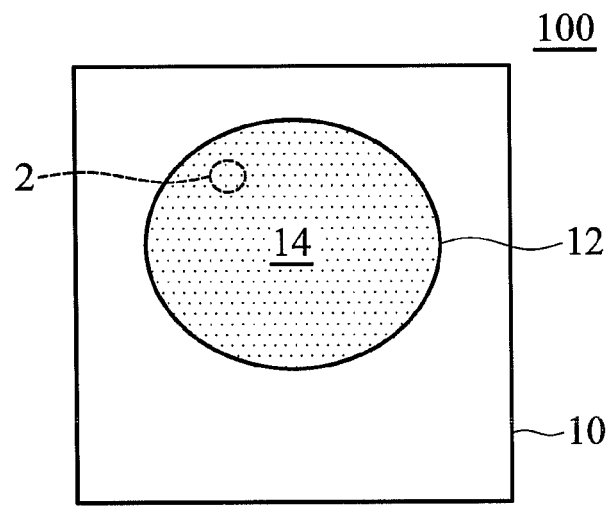
FIG. 1 shows a schematic diagram of the humidity indicator according to an embodiment of the disclosure.
Figure 2:
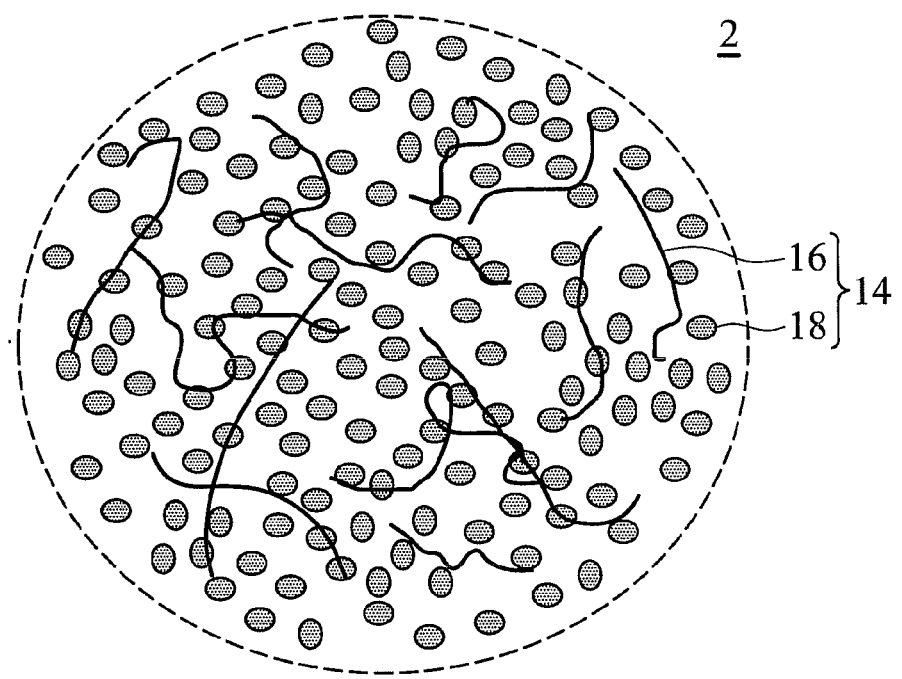
FIG. 2 shows a close-up schematic diagram of the location 2 of the composite 14 as shown in FIG. 1.
Figure 3:
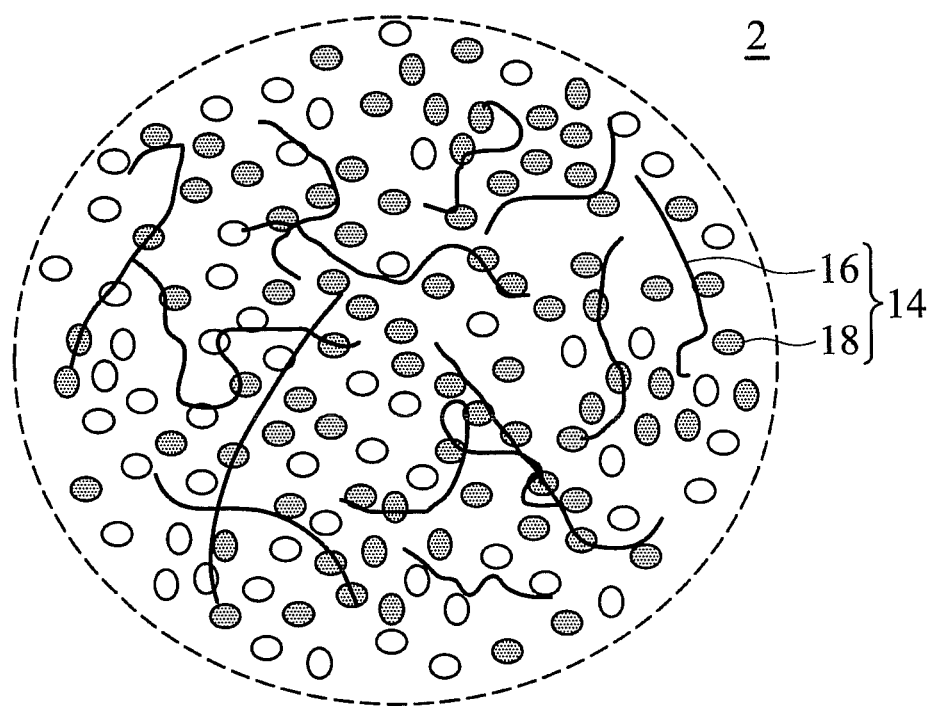
FIG. 3 shows a close-up schematic diagram of the location 2 of the composite 14 as shown in FIG. 1 after absorbing water.

Referring to FIG. 1, the humidity indicator 100 of the disclosure can include a substrate 10, wherein the substrate 10 has a region 12. A composite 14 is disposed in the region 12. FIG. 2 shows a close-up schematic diagram of the location 2 of the composite 14 as shown in FIG. 1. As shown in FIG. 2, the composite 14 includes the hydrophilic polymer 16, and the Ni-containing compound 18, wherein the Ni-containing compound 18 serve as a color change material for water, and the hydrophilic polymer can adjust the absorption efficiency of water due to the hydrophilic functional groups thereof. After the humidity indicator 100 absorbs the water from the surrounding environment, the Ni-containing compound 18 of the humidity indicator produces a color change from yellow-brown to blue, refer to FIG. 3, achieving the desired accuracy for determining humidity.

The substrate 10 of the disclosure can be a material with water impermeable property, high absorptivity, and quick-dry property, such as a plant pulp, chemical pulp, or combinations thereof. The Ni-containing compound 18 can be a Ni-containing salt, such as nickel sulfate, nickel acetate, nickel nitrate, nickel carbonate, nickel thiocyanate, nickel sulfide, or combinations thereof. The hydrophilic polymer 16 can include a hydrophilic functional group, wherein the hydrophilic functional group comprises a carboxylic acid group, ether group, hydroxyl group, ester group, or amide group. The hydrophilic polymer can be polyacrylic acid (PAA), polyacrylamide (PAM), polyvinyl alcohol (PVA), polyethylene glycol (PEG), polyethylene glycol diacid (PEG diacid), polyethylene glycol diacrylate (PEG diacrylate), or combinations thereof, and the hydrophilic polymer can have a molecular weight of between 150-5000.

It should be noted that, the water absorption efficiency of the humidity indicator depends on the weight ratio of the hydrophilic polymer and the Ni-containing compound. The weight ratio of the hydrophilic polymer and the Ni-containing compound can be modified according to a specific surrounding. In general, the weight ratio between the hydrophilic polymer and the Ni-containing compound can be of between 0.2 and 10. If the weight ratio between the hydrophilic polymer and the Ni-containing compound is more than 10, a non-uniform mixture state would be observed due to the poor intersolubility. To the contrary, if the weight ratio between the hydrophilic polymer and the Ni-containing compound is less than 0.2, the humidity indicator would exhibit poor color change.

Further, the disclosure also provides a method for fabricating the aforementioned humidity indicator. The method includes the following steps. First, a Ni-containing compound is dissolved into water to prepare an aqueous solution containing the Ni-containing compound, wherein the solid content (Ni-containing compound) of the aqueous solution is between 2~60 wt %.

Next, a hydrophilic polymer (or a solution containing the hydrophilic polymer) is added into the aqueous solution containing the Ni-containing compound to obtain a composition, wherein the weight ratio between the hydrophilic polymer and the Ni-containing compound is between 0.2 and 10. Next, the composition is coated on a predetermined region of a substrate and absorbed and fixed by the substrate. Next, the substrate is subjected to a pre-baking process at 50° C. for 30 min. Finally, the substrate is subjected to a baking process at 110-140° C. for a period of less than about 30 min, such as less than 10 min. The obtained humidity indicator can be reusable. After reusing the humidity indicator, the humidity indicator needs to be subjected to a baking process at 140° C. for 10-15 min in the absence of a pre-baking process.

The following examples are intended to illustrate the disclosure more fully without limiting the scope of the disclosure, since numerous modifications and variations will be apparent to those skilled in this art.

Example 1

First, 3.0 g of $NiSO_4$ was dissolved in 7.0 g of water, obtaining an $NiSO_4$(30 wt %) aqueous solution. Next, 3.3 g of PEG200 (poly(ethylene glycol), with a molecular weight of 200) was dissolved in water to obtain a PEG200 aqueous solution (with a PEG200 concentration of 0.2 g/ml). Next, the $NiSO_4$ aqueous solution was mixed with the PEG200 aqueous solution, and the mixture was stirred at 70° C. for 10 min, obtaining a composition (the weight ratio of $NiSO_4$ and PEG200 of 1.1:1). The composition was dropped in and absorbed by an indicator paper. The indicator paper was subjected to a pre-baking process at 50° C. for 30 min, and subjected to a baking process at 110° C. for 10 min, obtaining a humidity indicator.

Examples 2-3

Example 2 was performed in the same manner as in Example 1 except that the weight ratio of $NiSO_4$ and PEG200 was 1.7:1. Example 3 was performed in the same manner as in Example 1 except that the weight ratio of $NiSO_4$ and PEG200 was 0.2:1.

Example 4

The humidity indicators of Example 1-3 were set inside of a humidity chamber at a constant temperature, and an atmospheric exposure test was conducted for 60 min at a temperature of 23° C. and humidity of 50%. In the atmospheric exposure test, if the color change degrees of the humidity indicator in Examples are different, it means that the weight ratio of $NiSO_4$ and PEG200 has influenced the absorption efficiency of water.

Comparative Example 1

Comparative Example 1 was performed in the same manner as in Example 1 except for the absence PEG200.

Examples 5-7

Examples 5-7 were performed in the same manner as Examples 1-3, respectfully, except that the PEG400 (poly(ethylene glycol), with a molecular weight of 400) was used instead of the PEG200 in Examples 1-3.

Examples 8-10

Examples 8-10 were performed in the same manner as Examples 1-3, respectfully, except that the PEG4000 (poly(ethylene glycol), with a molecular weight of 4000) was used instead of the PEG200 in Examples 1-3.

Example 11

The humidity indicators of Comparative Example 1 and Example 5-10 were set inside of a humidity chamber at a constant temperature, and an atmospheric exposure test was conducted for 60 min at a temperature of 23° C. and humidity of 50%. The humidity indicator (without hydrophilic polymer) of Comparative Example 1 produced a color change after being set inside of the chamber for 45 min. On the other hand, the humidity indicators (including hydrophilic polymer) of Example 5-10 produced a color change after a half-hour of exposure. Accordingly, the presence of the hydrophilic polymer of the humidity indicator improves the absorption efficiency of water.

Further, the increased molecular weight of the hydrophilic polymer is apt to have a potential for causing a shielding effect, thereby extending the contact period between $NiSO_4$ and water. Therefore, the humidity indicator employing a relatively lower molecular weight exhibited higher hydrophilicity and faster absorption efficiency of water. Accordingly, the humidity indicator of the disclosure preferably employs a hydrophilic polymer with a molecular weight of between 150-5000.

Examples 12-17

Example 12 was performed in the same manner as in Example 1 except that the PEG diacid 600 (polyethylene glycol diacid, with a molecular weight of 600) was used instead of the PEG200 in Example 1. Example 13 was performed in the same manner as in Example 1 except that the PEG diacrylate 575 (polyethylene glycol diacrylate, with a molecular weight of 575) was used instead of the PEG200 in Example 1. Example 14 was performed in the same manner as in Example 1 except that the PEG2000 (polyethylene glycol, with a molecular weight of 2000) was used instead of the PEG200 in Example 1. Example 15 was performed in the same manner as in Example 1 except that the PVA2000 (poly(vinyl alcohol), with a molecular weight of 2000) was used instead of the PEG200 in Example 1. Example 16 was performed in the same manner as in Example 1 except that the PA1800 (polyacrylate, with a molecular weight of 1800) was used instead of the PEG200 in Example 1. Example 17 was performed in the same manner as in Example 1 except that the PAM1500 (poly(acrylamide), with a molecular weight of 1500) was used instead of the PEG200 in Example 1.

Example 18

The humidity indicators of Comparative Example 1 and Examples 12-17 were set inside of a humidity chamber at a constant temperature, and an atmospheric exposure test was conducted for 60 min at a temperature of 23° C. and humidity of 70%. The colour difference (%) of the humidity indicators was measured by a chromameter (MINOLTA CM 508) with a CIE illuminant D65)(10°, and the results are shown in Table 1.

TABLE 1

| | Comparative Example 1 | Example 12 | Example 13 | Example 14 | Example 15 | Example 16 | Example 17 |
|---|---|---|---|---|---|---|---|
| colour difference (%) | 0.3 | 2.64 | 3.28 | 0.98 | 2.54 | 1.76 | 0.15 |

As shown in Table 1, the hydrophilic polymers used in Examples 12-17 facilitated the absorption efficiency of the humidity indicators.

Examples 19-24

Examples 19-24 were performed in the same manner as in Example 1 except that an $Ni(SCN)_2$ saturated aqueous solution was used instead of the $NiSO_4$ aqueous solution in Example 1.

Example 25

The humidity indicators of Examples 19-24 were set inside of a humidity chamber at a constant temperature, and an atmospheric exposure test was conducted for 60 min at a temperature of 23° C. and humidity of 70%. The colour difference (%) of the humidity indicators was measured, and the results are shown in Table 2.

TABLE 2

| | Example 19 | Example 20 | Example 21 | Example 22 | Example 23 | Example 24 |
|---|---|---|---|---|---|---|
| colour difference (%) | 2.43 | 13.04 | 3.83 | 2.1 | 4.62 | 3.29 |

As shown in Table 2, the humidity indicators including $Ni(SCN)_2$ had a more obvious color change in comparison with the humidity indicators including $NiSO_4$. Further, the humidity indicator including $Ni(SCN)_2$ and PEG diacrylate had the most obvious color changes.

The humidity indicators of the disclosure are reusable, halide-free, and cobalt-free, meeting the requirement of environmental friendliness. Further, as shown in Table 3, the humidity indicators of the disclosure have high colour difference, and can be used in a range of 5-60% RH for accurately determining humidity. The hydrophilic polymer and the Ni-containing compound of the humidity indicator can be optionally selected according to the object of use. Moreover, the method for fabricating the humidity indicators of the disclosure has the advantages of reduced equipment requirement, easy process, cheap, and, excellent controllability.

TABLE 3

| Sample | A | B | C | D | E |
|---|---|---|---|---|---|
| Ni-containing compound | $Ni(SCN)_2$ | $Ni(SCN)_2$ | $Ni(SCN)_2$ | $Ni(SO_4)$ | $Ni(NO_3)_2$ |
| Ni concentration | 5% | 5% | 5% | 30% | 20% |
| polymer | PEG diacid 600 | PEG diacrylate 575 | — | — | PEG 2000 |
| Polymer concentration | 0.2 g/ml | 0.2 g/ml | — | — | 0.2 g/ml |
| Ni/polymer | 1:1 | 1:1 | — | — | 1:1 |
| | | | Color change | | |
| RH(%)  0 | — | brown | brown | yellow | brown |
| 5 | blue-green | green | yellow-green | yellow | brown |
| 10 | green-blue | blue-green | green | yellow | brown |
| 55 | blue | blue | blue | blue | green-yellow |

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A humidity indicator, comprising:
   a substrate; and
   a composite disposed on a predetermined region of the substrate, wherein the composite is a mixture comprising a hydrophilic polymer, and a Ni-containing compound.

2. The humidity indicator as claimed in the claim 1, wherein the weight ratio between the hydrophilic polymer and the Ni-containing compound is between 0.2 and 10.

3. The humidity indicator as claimed in the claim 1, wherein the Ni-containing compound comprises nickel sulfate, nickel acetate, nickel nitrate, nickel carbonate, nickel thiocyanate, nickel sulfide, or combinations thereof.

4. The humidity indicator as claimed in the claim 1, wherein the hydrophilic polymer comprises a hydrophilic functional group, wherein the hydrophilic functional group comprises a carboxylic acid group, ether group, hydroxyl group, ester group, or amide group.

5. The humidity indicator as claimed in the claim 4, wherein the hydrophilic polymer comprises polyacrylic acid (PAA), polyacrylamide (PAM), polyvinyl alcohol (PVA), polyethylene glycol (PEG), polyethylene glycol diacid (PEG diacid), polyethylene glycol diacrylate (PEG diacrylate), or combinations thereof.

* * * * *